United States Patent [19]

Maurin et al.

[11] Patent Number: 4,866,088

[45] Date of Patent: Sep. 12, 1989

[54] PREPARATION PROCESS FOR AN AQUEOUS PHARMACEUTICAL SOLUTION OF AN ACTIVE PRINCIPLE CONSTITUTED BY AN ORGANIC ACID

[75] Inventors: Florence Maurin, Pignan; Claude Coquelet, St Gely du Fese; Tournoux A. Alain, Montpellier, all of France

[73] Assignee: Laboratoires Chauvin-Blache, France

[21] Appl. No.: 40,015

[22] Filed: Apr. 20, 1987

[30] Foreign Application Priority Data

Apr. 30, 1986 [FR] France ................................ 86 06346

[51] Int. Cl.$^4$ ............................................ A61K 31/40
[52] U.S. Cl. ...................................................... 514/420
[58] Field of Search ............................................ 514/420

[56] References Cited

U.S. PATENT DOCUMENTS

3,193,459  7/1965  Korman et al. ...................... 514/180

FOREIGN PATENT DOCUMENTS

0076658  9/1982  European Pat. Off. .
2428226  6/1974  Fed. Rep. of Germany .
3507024  2/1985  Fed. Rep. of Germany .
2059768  9/1980  United Kingdom .

OTHER PUBLICATIONS

Chemical Abstracts, vol. 99, No. 24, Dec., 1983, p. 342, no. 200541h Search Report for application FR-8-6-063436.

*Primary Examiner*—Stanley J. Friedman
*Attorney, Agent, or Firm*—Wegner & Bretschneider

[57] ABSTRACT

Buffered opthalmic solutions of indomethacin.

9 Claims, No Drawings

PREPARATION PROCESS FOR AN AQUEOUS PHARMACEUTICAL SOLUTION OF AN ACTIVE PRINCIPLE CONSTITUTED BY AN ORGANIC ACID

DESCRIPTIVE SUMMARY

The subject of the invention is a preparation process for an aqueous pharmaceutical solution of an active principle constituted by an organic acid, characterized in that:

(a) the organic acid is dissolved in a first aqueous solution containing a sufficient quantity of at least a fraction of the basic part of a buffer mixture (b) this solution is lyophilized in order to obtain a product in a dry state and (c) at the time of use the product in a dry state is dissolved in a second aqueous solution containing the remainder of the buffer mixture, this remainder being such that the pH of the resulting solution is of a physiologically acceptable value.

The present invention is concerned with a preparation process for an aqueous pharmaceutical solution of an active principle constituted by an organic acid normally considered as very slightly soluble or insoluble in water.

The present invention is concerned more particularly with a preparation process for an aqueous pharmaceutical solution which contains notable quantities of such an active principle (generally from 0.05 to 5% by weight) and which is stable for at least one mouth in normal conditions of use. It is concerned in particular with a preparation process for ophthalmic solutions.

Various attempts have already been made to make soluble active principles which are very slightly soluble or insoluble in water. There can be cited in particular the following methods:

(1) Micellar system of making soluble

The micellization system allows hydrophobic substances to be made soluble in water but the active principle dissolved in this way risks being much less stable (alteration or hydrolysis) than in systems where it is insoluble. Furthermore the active principle is susceptible to losing a part of its biological activity. This system therefore does not resolve the general pharmaceutical problem of administration of a product insoluble in water in normal conditions.

(2) Making soluble by co-solvent (see for example application PCT WO 85/04106)

Hydrophobic products are susceptible to being made soluble by cosolvents of the polyethyleneglycol type (PEG) of various molecular weights or other similar solvents, but the active principle is then susceptible to forming complexes of the ester type of PEG or to become hydrolized by the traces of water present in the co-solvent, therefore not guaranteeing the stability required for the formulation of a pharmaceutical speciality.

(3) Putting the active principle in suspension (see for example U.S. Pat. No. 4 087 538)

The stabilizing of a suspension of an active principle in a micronized form is obtained by the presence of a suspension agent, namely one or more tensio-active agents of mono-oleate type of polyoxyethylene sorbitan (Tween 80) or other esters of sorbitan, particularly of lauric acid and of stearic acid, which enables the fraction made soluble by water to become micellised. Such suspensions, by the presence of the micronized particles, cause an ocular intolerance and are not suitable in the field of ophthalmics.

The present invention is concerned with remedying these inconveniences.

The present invention is based on the discovery that it is possible to dissolve an organic acid which is normally very slightly soluble in water such as indomethacin in an aqueous solution containing a sufficient quantity of at least the basic part of a buffer mixture and that the quantity of organic acid that can be dissolved is the greater, the larger the quantity of the basic part of the buffer mixture.

The subject of the present invention is therefore a preparation process for an aqueous pharmaceutical solution with an active principle constituted by an organic acid, characterized in that (a) the organic acid is dissolved in a first aqueous solution containing a sufficient quantity of at least a fraction of the basic part of a buffer mixture, (b) this solution is lyophilized in order to obtain a product in a dry state and (c) at the time of use the product in a dry state is dissolved in a second aqueous solution containing the remainder of the buffer mixture, this remainder being such that the pH of the resulting solution is of a physiologically acceptable value.

Thus in the first stage of the process according to the present invention the organic acid is dissolved in a first aqueous solution containing a sufficient quantity of at least a fraction of the basic part of the buffer mixture. This first solution generally also contains a fraction of the acid part of the buffer mixture in such a way as to be close to neutrality and to avoid pH values which are too basic and capable of affecting the stability of the active principle, whilst the second solution contains the remainder of the acid part of the buffer mixture and can also contain a fraction of the basic part of the buffer mixture.

At the limit, the first solution could even contain the total amount of the constituents of the buffer mixture. However, in this case, the solubility of the organic acid remains fairly weak. In addition it is advantageous to be able to adjust the pH of the final solution to the desired value for administration, thanks to the presence of the remainder of the acid part of the buffer mixture in the second solution. Generally the pH values close to neutrality (pH of 6.5 to 7.5) are desirable for administration to man and to animals.

The buffer mixtures that can be used in the present invention are in particular the following:
Boric acid-sodium borate buffer
Monosodium phosphate-disodium phosphate buffer
Monopotassium phosphate-dipotassium phosphate buffer
Acetic acid-sodium acetate buffer
Citric acid-sodium citrate acid and mixtures of these buffers. The first three buffers are preferred.

In order to decrease the global quantity of the buffer mixture, volatile co-solvents such as ethanol can be added to the first solution. Such an addition of ethanol (not exceeding in general 10% by volume) is useful especially when it is desired to obtain solutions to be lyophilized having significant concentrations of active principle (for example of more than 2% by weight).

The first solution can in addition contain any antibacterial agent capable of guaranteeing the bacteriological quality of the solutions, as for example esters of parahydroxybenzoic acid, and/or any stabilizer of antioxidant type such as sodium sulphites and derivatives, or edetic acid and its salts, as well as any other active principle soluble in water which is capable of completing or improving the therapeutic activity of the first. In addition for ophthalmic applications the solution can contain any product capable of prolonging the contact time and/or of improving the corneal penetration of the active principle, and in particular compounds of dextran type, cellulose derivatives or other thickening agents compatible with the ophthalmic form of the speciality.

The solution thus prepared is sufficiently stable to allow its lyophilization, which is carried out according to the usual methods.

Lyophilization presents the advantage of producing a product which can be kept for a long time. The absence of water and of any co-solvent such as a polyethyleneglycol avoids in effect any degradation or modification of the active principle. In addition the co-solvents which can be used are eliminated by sublimation during lyophilization, so that these co-solvents do not interfere even for an ophthalmic application.

At the time of use the lyophilized product is dissolved in the second solution containing the remainder of the buffer mixture, that is to say in general the remainder of the acid part of the buffer.

This second solution comprises in general from 75 to 98% by weight of water. It can contain any water soluble antibacterial agent, any water soluble antioxidant substance; any other active principle soluble and stable in water; any substance capable of stabilizing the pH at a value compatible with the ocular tolerance: any product having an influence on the tonicity of the solution like sodium chloride, glycocoll, glucose; any substance capable of stabilizing the active principle in an aqueous solution. As stabilizers there can be used in particular polyethyleneglycols of which the molecular weight can be from 200 to 1500 and in particular from 200 to 600, at a rate of 0 to 25% by weight.

The risks of modification of the active principle by the PEG contained in the second solution, and this after reconstitution, are thus much less significant than for a solution in pure PEG because of the large proportion of water in the second solution. Other stabilizers can also be used such as propylene glycol, tetrahydrofurfuryl polyethyleneglycol.

The present invention applies to the preparation of aqueous solutions of active principles constituted by organic acids and in particular aryl or heterocyclic compounds with a carboxylic acid group such as indomethacin, aspirin, niflumic acid, ibuprofen, pranoprofen, ketoprofen, alminoprofen, naproxen, sulindac.

The present invention finds a particularly useful application in the preparation of aqueous ophthalmic solutions of indomethacin.

In the case of aqueous ophthalmic solutions of indomethacin there is advantageously prepared in a first stage a solution containing from 0.1 to 7.5% by weight of indomethacin anda sufficient quantity of a fraction of a buffer mixture containing at least a fraction of the basic part of the buffer mixture and in general a fraction of the acid part of this mixture, this solution having a pH of 6.5 to 7.5 and preferably of 6.8 to 7.2. Such a pH is favourable to the stability of the indomethacin. A co-solvent such as ethanol can be added in a quantity which can go up to 10% by weight when the concentration of indomethacin is greater than 2% by weight in the solution. This solution is lyophilized and in addition a second solution is prepared containing the remainder of the buffer mixture. This second solution generally has a pH of 4.5 to 6.5 and, by the dissolving of the lyophilized product in this second solution, enables a resultant solution to be obtained, which has a final pH compatible with the eye, generally from 6.5 to 7.5 and advantageously from 6.8 to 7.3. This ophthalmic solution can generally have a concentration of indomethacin of 0.05 to 1% by weight.

It should be noted that if the boric acid-sodium borate buffer is used the quantity by weight of indomethacin that can be dissolved in the first solution is approximately equal to the quantity (by weight) of sodium borate.

The present invention applies not only to the preparation of ophthalmic solutions but also to the preparation of nasal solutions, of injectable solutions and of drinkable solutions.

The following examples illustrate the present invention.

EXAMPLE 1

Preparation of a collyrium containing 0.1% by weight of ndomethacin and a borate buffer A first solution of indomethacin is prepared by agitation at ambient temperature of the following constituents:

| | |
|---|---|
| indomethacin | 0.250 g |
| sodium borate | 0.255 g |
| boric acid | 1.405 g |
| dextran | 1.000 g |
| water q.s. for | 100.000 ml |

This solution has a pH of 7.0.

This solution is lyophilized immediately, after having divided it into flasks each containing 2 ml of solution.

A second solution is prepared in addition by mixing at ambient temperature the following constituents:

| | |
|---|---|
| boric acid | 1.149 g |
| nipagin (preservative) | 0.050 g |
| PEG 400 (stabilizer) | 24.850 g |
| water q.s. for | 100.000 ml |

The pH of this solution is 5.65.

This solution is divided into flasks each containing 5 ml.

At the time of use 5 ml of the second solution contained in one flask of solution is added to the lyophilized product contained in another flask. A collyrium containing 0.1% by weight of indomethacin is obtained, having a pH of 7.1.

This solution has, remarkably, a preservation time of at least one month at ambient temperature.

EXAMPLE 2

Preparation of a collyrium containing 0.1% by weight of indomethacin

The operating method is as for example 1, using the following solutions:

| First solution (to be lyophilized) divided into flasks each containing 2 ml. | |
|---|---|
| indomethacin | 0.250 g |
| dextran | 1.000 g |

-continued

| | |
|---|---|
| monosodium phosphate | 0.612 g |
| disodium phosphate | 6.400 g |
| nipagin | 0.125 g |
| water q.s. for | 100.000 ml |
| pH | 7.25 |

| Second solution, divided into flasks each containing 5 ml | |
|---|---|
| monosodium phosphate | 0.874 g |
| PEG 400 | 10.000 g |
| water q.s. for | 100.000 ml |
| pH | 5.1 |

The final collyrium has a pH of 7.1 and is stable for at least one month.

EXAMPLE 3

Preparation of a collyrium containing 0.4% by weight of indomethacin

The operating method is as for example 1, using the following solutions:

| First solution (to be lyophilized) divided into flasks each containing 2 ml | |
|---|---|
| indomethacin | 1.000 g |
| dextran | 1.000 g |
| boric acid | 2.180 g |
| sodium borate | 1.000 g |
| water q.s. for | 100.000 ml |
| pH | 7.0 |

| Second solution (divided into flasks each containing 5 ml) | |
|---|---|
| boric acid | 1.500 g |
| PEG 400 | 25.000 g |
| water q.s. for | 100.000 ml |
| pH | 5.55 |

The final collyrium has a pH of 7.1 and is stable for at least two months.

EXAMPLE 4

Preparation of a collyrium containing 0.1% by weight of ibuprofen

The operating method is as for example 1, using the following solutions:

| First solution (to be lyophilized) divided into flasks each containing 2 ml | |
|---|---|
| ibuprofen (acid) | 0.250 g |
| nipagin | 0.125 g |
| boric acid | 2.190 g |
| sodium borate | 0.500 g |
| dextran | 1.000 g |
| water q.s. for | 100.000 ml |
| pH | 7.0 |

| Second solution (divided into flasks each containing 5 ml) | |
|---|---|
| boric acid | 1.224 g |
| PEG 400 | 25.000 g |
| water q.s. for | 100.000 g |
| pH | 5.6 |

The final collyrium has a pH of 7.0 and is stable for at least one month.

EXAMPLE 5

Collyrium containing 0.1% by weight of indomethacin

The operating method is as for example 1.

| First solution: | |
|---|---|
| indomethacin | 0.250 g |
| ethanol | 5.000 ml |
| sodium borate | 0.1315 g |
| boric acid | 0.450 g |
| nipagin | 0.125 g |
| dextran | 5.000 g |
| water q.s. for | 100.000 ml |
| pH | 7.0 |
| Second solution: | |
| sodium borate | 0.018 g |
| boric acid | 0.727 g |
| PEG 400 | 24.85 g |
| water q.s. for | 100.000 ml |
| pH | 7.2 |
| pH of final collyrium | 7.2 |

EXAMPLE 6

Collyrium containing 0.4% by weight of indomethacin

The operating method is as for example 1.

| First solution: | |
|---|---|
| indomethacin | 1.000 g |
| sodium borate | 1.000 g |
| boric acid | 2.180 g |
| dextran | 1.000 g |
| water q.s. for | 100.000 ml |
| pH | 7.0 |
| Second solution: | |
| boric acid | 1.500 g |
| nipagin | 0.050 g |
| PEG 600 | 25.000 g |
| water q.s. for | 100.000 ml |
| pH | 5.5 |
| pH of final collyrium | 7.0 |

EXAMPLE 7

Collyrium containing 0.1% by weight of indomethacin

The operating method is as for example 1.

| First solution: | |
|---|---|
| indomethacin | 0.250 g |
| sodium borate | 0.255 g |
| boric acid | 1.405 g |
| dextran | 1.000 g |
| water q.s. for | 100.000 ml |
| pH | 7.0 |
| Second solution: | |
| boric acid | 1.149 g |
| nipagin | 0.050 g |
| PEG 400 | 5.000 g |
| water q.s. for | 100.000 ml |
| pH | 5.7 |
| pH of final collyrium | 7.0 |

EXAMPLE 8

Collyrium containing 2% by weight of indomethacin

The operating method is as for example 1.

| First solution: | |
|---|---|
| indomethacin | 5.000 g |
| ethanol | 5.000 ml |
| sodium borate | 5.000 g |
| boric acid | 2.140 g |
| dextran | 1.000 g |
| water q.s. for | 100.000 g |
| pH | 7.2 |

-continued

| Second solution: | |
|---|---|
| boric acid | 2.452 g |
| PEG 400 | 25.000 g |
| nipagin | 0.050 g |
| water q.s. for | 100.000 ml |
| pH | 5.2 |
| pH of final collyrium | 7.0 |

EXAMPLE 9

Preparation of a collyrium containing 0.1% of indomethacin

The operating method is as for example 1, in such a way as to obtain per flask the following formula of the lyophilisate.

| indomethacin | 5 mg |
|---|---|
| borax | 5.1 mg |
| boric acid | 28.096 mg |
| dextran | 20 mg |

In addition the following solution is prepared:

| PEG 400 | 1242.5 mg |
|---|---|
| nipagin | 2.5 mg |
| EDTA | 2.5 mg |
| boric acid | 99.75 mg |
| borax | 7.45 mg |
| purified water q.s. for | 5 ml |

At the time of use the solution constituting the solvent is added to the lyophilisate and a reconstituted collyrium is obtained having the following percentage formula:

| indomethacin | 0.1 g |
|---|---|
| borax | 0.251 g |
| boric acid | 2.5569 g |
| nipagin | 0.05 g |
| EDTA | 0.05 g |
| PEG 400 | 24.85 g |
| dextran | 0.4 g |
| purified water q.s. for | 100 ml |

What is claimed is:

1. A process for the preparation of an ophthalmic solution of indomethacin by using a buffer mixture composed of a basic part and an acidic part, the buffer mixture being selected from the group consisting of boric acid-sodium borate buffer, monosodium phosphate-disodium phosphate buffer, monopotassium phosphate-dipotassium phosphate buffer, acetic acid-sodium acetate buffer, citric acid-sodium citrate buffer, and mixtures of these buffers, wherein
   (a) a first aqueous solution is prepared containing 0.1 to 7.5% by weight of indomethacin and a solubilizing quantity of at least a fraction of the basic portion of the buffer mixture, said fraction providing to this first solution a pH value in the range of from 6.5 to 7.5,
   (b) the resultant solution is lyophilized in order to obtain a dry product, and
   (c) at the time of use the dry product is redissolved in a second aqueous solution which contains the remainder of the buffer mixture, this remainder providing to the resultant aqueous ophthalmic solution a pH value in the range of from 6.5 to 7.5.

2. Process according to claim 1, in which the first solution contains up to 10% by weight of ethanol.

3. Process according to claim 1, in which the second solution has a pH of 4.5 to 6.5.

4. Process according to claim 1, in which the first solution also contains a fraction of the acid portion of the buffer mixture, and the second solution contains the remainder of the buffer mixture.

5. Process according to claim 1, in which the buffer mixture employed is selected from the group consisting of the following buffer mixtures, namely boric acid-sodium borate, monosodium phosphate-disodium phosphate and monopotassium phosphate-dipotassium phosphate.

6. Process according to claim 1, in which the first solution contains a volatile co-solvent.

7. Process according to claim 6, in which the co-solvent is ethanol.

8. Process according to claim 1, in which the second solution contains a stabilizer.

9. Process according to claim 8, in which the stabilizer is a polyethyleneglycol having a molecular weight in the range of from 200 to 1500.

* * * * *